United States Patent [19]

Hosoda et al.

[11] Patent Number: 5,173,406
[45] Date of Patent: Dec. 22, 1992

[54] LIPOSOME IMMUNOASSAY METHOD AND KIT THEREFOR

[75] Inventors: Kenji Hosoda, Kawagoe; Hideaki Suzuki, Koganei; Tatsuji Yasuda, Yokohama, all of Japan

[73] Assignee: Teijin Limited, Osaka, Japan

[21] Appl. No.: 339,824

[22] PCT Filed: Apr. 28, 1988

[86] PCT No.: PCT/JP88/00435
§ 371 Date: Jan. 5, 1989
§ 102(e) Date: Jan. 5, 1989

[87] PCT Pub. No.: WO88/08982
PCT Pub. Date: Nov. 17, 1988

[30] Foreign Application Priority Data

May 6, 1987 [JP] Japan .................. 62-108844

[51] Int. Cl.⁵ .................. G01N 33/542; G01N 33/544
[52] U.S. Cl. .................. 435/7.72; 435/7.9; 435/966; 435/968; 435/975; 436/528; 436/537; 436/800; 436/805; 436/821; 436/829
[58] Field of Search .................. 435/7.72, 968, 7.9, 435/975, 966; 436/537, 800, 805, 829, 821. 528

[56] References Cited

U.S. PATENT DOCUMENTS

| | | | |
|---|---|---|---|
| 4,447,529 | 5/1984 | Greenquist et al. | 435/7 |
| 4,495,296 | 1/1985 | Neurath et al. | 436/541 X |
| 4,971,916 | 11/1990 | Jou et al. | 436/818 X |

FOREIGN PATENT DOCUMENTS

| | | |
|---|---|---|
| 144084 | 6/1985 | European Pat. Off. |
| 60-138465 | 7/1985 | Japan . |
| 60-138466 | 7/1985 | Japan . |
| 60-159652 | 8/1985 | Japan . |
| 61-250558 | 11/1986 | Japan . |
| 61-250560 | 11/1986 | Japan . |
| 61-269070 | 11/1986 | Japan . |

OTHER PUBLICATIONS

"Homogeneous Immunoassay for $\alpha_2$ Plasmin Inhibitor ($\alpha_2$ PI) and $\alpha_2$ PI–plasmin Complex", by K. Hosoda et al., Journal of Immunological Methods, vol. 121, (1989), pp. 121–128.
Umada et al., J. Immunol. Meth., 95:15, 1986.
Bio-Industry, vol. 3, No. 7, 1986, pp. 566–571, T. Yasuda.

Primary Examiner—David Saunders
Attorney, Agent, or Firm—Sughrue, Mion, Zinn, Macpeak & Seas

[57] ABSTRACT

A liposome immunoassay comprising the steps of reacting an analyte antigen, a liposome bearing antibody comprising a first antibody to the analyte antigen and a liposome encapsulating a marker therein linked to the antibody, and a second antibody to the analyte antigen to form an antigen-antibody complex, releasing the marker from the liposome in an amount depending on an amount of the analyte antigen in the presence of a complement, and measuring the released marker to determine the analyte antigen, characterized in using a third antibody capable of binding directly or indirectly to the second antibody and having an ability to activate the complement; and A kit for liposome immunoassay comprising at least one of; (1) an liposome bearing antibody comprising a first antibody to an analyte antigen and liposome encapsulating a marker therein linked to the antibody; (2) a second antibody to the analyte antigen; (3) a third antibody capable of binding directly or indirectly to the second antibody and having an ability to activate a complement; and (4) the complement.

16 Claims, 6 Drawing Sheets

LIPOSOME IMMUNOASSAY METHOD AND KIT THEREFOR

DESCRIPTION

1. Technical Field

The present invention relates to a liposome immunoassay method and kit therefor.

2. Background Art

In the medical field, immunoassay methods involving an antigen-antibody reaction are now often used for the diagnosis of diseases, etc. Although conventional immunoassays are generally classified as heterogeneous assays and homogeneous assays, the homogeneous assay, in which a washing operation is unnecessary, has become increasingly important due to the suitability to diseases and the ease of diagnosis obtained thereby. Nevertheless, most homogeneous assays do not have a satisfactory sensitivity.

Accordingly, various liposome immunoassay methods have been proposed, with the intention of improving this sensitivity. In these methods, an antigen-antibody complex is formed by a reaction of an antigen as an analyte and a liposome bearing antibody comprising an antibody to the analyte antigen and a liposome encapsulating a marker therein linked to the antibody, the marker is released from the liposome in a complement-dependent manner, and the released marker is measured to determine the analyte antigen.

As an embodiment of such a liposome immunoassay, a method is known wherein three entities, i.e., an antigen as an analyte, a liposome bearing antibody comprising a first antibody to the antigen and a liposome encapsulating a marker therein linked to the antibody, and a second antibody to the analyte antigen are reacted to form an antigen-antibody complex of three components, a complement is added to this complex of three components to release the marker from the complexed liposome, and the released marker is measured to determine the analyte antigen. As an embodiment of such an liposome immunoassay, Japanese Unexamined Patent Publication No. 60-138465 discloses a method which uses antibodies derived from different species as the first and second antibodies. Japanese Unexamined Patent Publication No. 61-250558 describes a method similar to the above-method, wherein a hydrophilic marker is encapsulated in a liposome comprising at least one of phospholipide and glycolipide and cholesterol, and the liposome to which at least a part of an antibody to a test substance is used. Japanese Unexamined Patent Publication No. 61-269070 describes a general method similar to the above method. Moreover, Japanese Unexamined Patent Publication No. 61-250560 discloses a liposome immunoassay characterized by reacting four entities, i.e., a first antibody to an analyte antigen, a conjugate of a second antibody to the first antibody and a liposome encapsulating a marker substance, a third antibody to the analyte antigen, and a complement.

In all of the above methods, an antibody, which satisfies two requirements, i.e., (1) is capable of specifically reacting with the analyte antigen, and (2) is capable of activating the complement, must be used as the second or third antibody, but it is not easy to obtain an antibody which satisfies these requirements.

Accordingly, the present invention is intended to resolve the above problems by using different antibodies; one responsible for the first requirement, i.e., the reactivity with the analyte antigen, and another responsible for the second requirement, i.e., ability to activate the complement, and binding these antibodies specifically to each other.

DISCLOSURE OF THE INVENTION

The above-mentioned problems are resolved by the present liposome immunoassay comprising the steps of reacting an analyte antigen, a liposome bearing antibody comprising a first antibody to the analyte antigen and a liposome encapsulating a marker therein linked to the antibody, and a second antibody to the analyte antigen, to form an antigen-antibody complex, releasing the marker from the liposome in an amount depending on an amount of the analyte antigen in the presence of a complement, and measuring the released marker to determine the analyte antigen, characterized in using a third antibody capable of binding directly or indirectly to the second antibody and having an ability to activate the complement.

The present invention also provides a kit for liposome Immunoassay comprising at least one of:

(1) an liposome bearing antibody comprising a first antibody to an analyte antigen and liposome encapsulating a marker therein linked to the antibody;

(2) a second antibody to the analyte antigen;

(3) a third antibody capable of binding directly or indirectly to the second antibody and having an ability to activate a complement; and (4) the complement.

BEST MODE OF CARRYING OUT THE INVENTION

Figure 1:
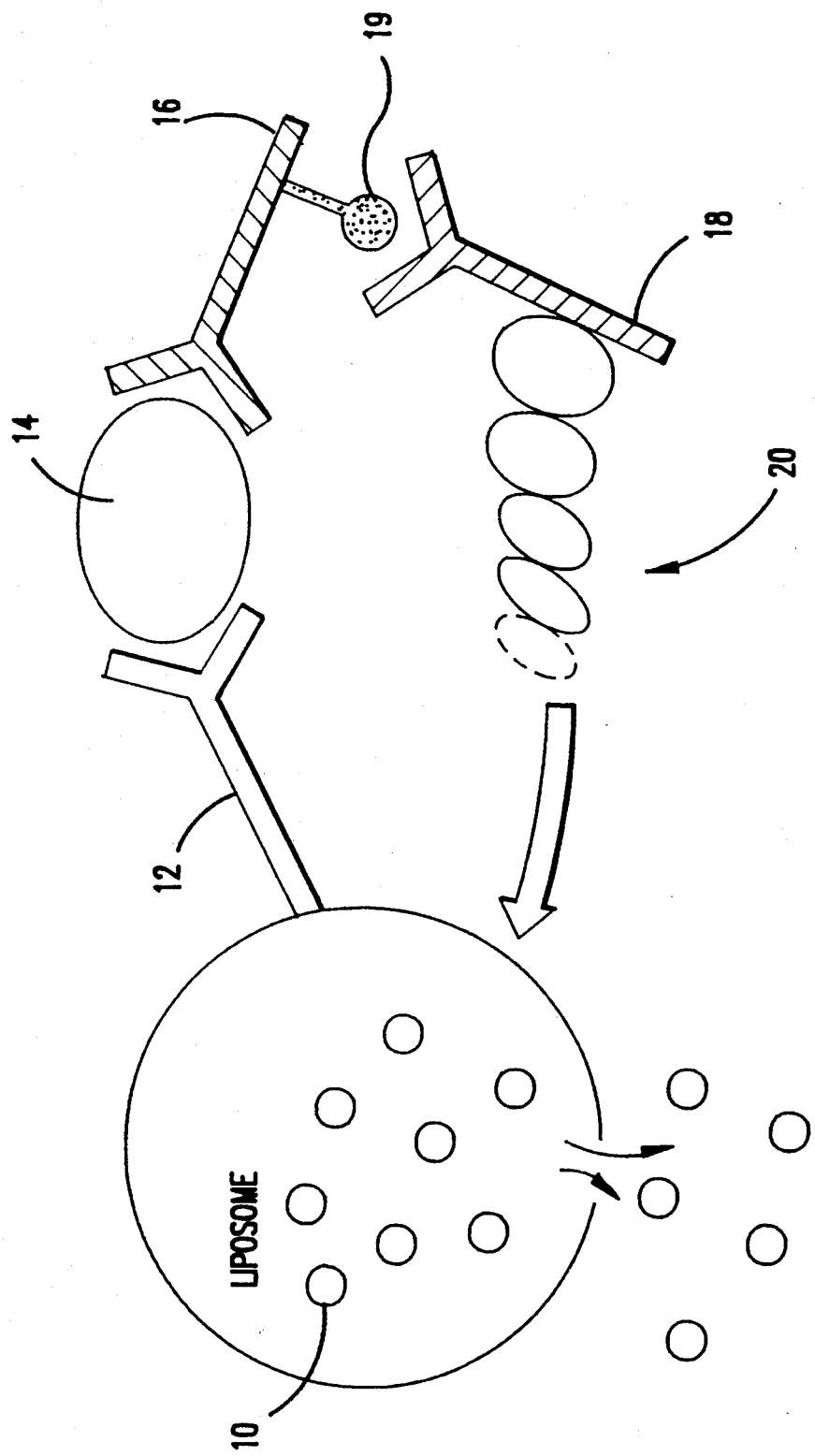
FIG. 1 is a schematic drawing showing a principle of the present liposome immunoassay, wherein 10 represents encapsulated marker; 12 represents a first antibody; 14 represents an analyte antigen; 16 represents a second antibody; 18 represents a third antibody; 19 represents a hapten; and 20 represents complements.

A principle of the present liposome immunoassay is schematically represent in FIG. 1. In the present invention, (1) an analyte antigen, (2) a liposome bearing antibody comprising a first antibody to the analyte antigen and a liposome encapsulating a marker substance therein linked to the antibody, (3) a second antibody to the analyte antigen, and a third antibody capable of binding directly or indirectly to the second antibody and capable of activating a complement, are reacted to form an antigen-antibody complex. In this manner, the antigen-antibody complex is formed in an amount depending on an amount of the analyte antigen. By acting the complement on the complex, the complement is activated by the action of the third antibody in the complex, and by the action of the activated complement on the surface of the liposome, the liposome is broken resulting in a release of the marker substance encapsulated in the liposome. Accordingly, the analyte antigen can be measured by measuring the released marker substance.

Therefore, according to the present method, since different antibodies are responsible for the ability to bind to the analyte antigen and ability to activate the complement, which are necessary for the release of the marker substance from the liposome, the antibodies can be easily obtained, and the method can be applied to various kinds of analytes.

The present assay system can be applied to the measurement of various kinds of substances. For example, antigens preferably measured according to the present invention include coagulation-fibrinolysis elements, such as $\alpha_2$ plasminogen inhibitor ($\alpha_2$PI), $\alpha_2$PI-plasmin complex, protein C, protein S, plasminogen, tissue plasminogen activator (TPA), TPA inhibitor (TPA I), TPA-TPA I complex, antithrombin III (AT III), AT III-thrombin complex, fibrinopeptide A, $B\beta15$-42. Moreover, cancer markers, such as $\alpha$-fetoprotein, carcinoembryotic antigen (CEA), glutathione S-transferase (GST-$\pi$); an inflammation marker such as C reactive protein (CRP); hormones such as human chorionic gonadotropin ($\beta$HCG); luteinizing hormone, (LH), follicle-stimulating hormone-releasing factor (FSH); an osteometabolism-related substance such as osteocalcin, bone alkaline phosphatase; or an immune-related substance such as interleukins 1 to 6, and tumor necrosis factor, and the like can be measured.

Liposomes used in the present invention may be various kinds of conventional liposomes having a known composition and process for preparation. For example, phospholipids such as choline, phosphatidylcholine, sphingomyelin, phosphatidic acid, phosphatidyl serine, as constitutional ingredients; cholesterols as a stabilizer; and dithiopyridyl group substituted or maleimid group substituted phosphatidyl ethanolamine (cross-linking phospholipide) are used. For example, a liposome suspension can be obtained by dissolving phosphatidyl choline, cholesterol, and dithiopyridyl group substituted phosphatidylethanol amine in a solvent, evaporating the solvent under a reduced pressure, adding an aqueous medium to the residue, and stirring the mixture with a vortex mixer or the like.

As markers used in the present invention, any markers conventionally used in immunoassays and having a known detection and measurement can be used. For example, methods wherein an enzyme such as glucose-6-phosphate dehydrogenase is used as a marker, and visible, fluorescent or ultraviolet rays developed from an enzyme substrate are measured; methods wherein a fluorescent substance such as carboxyfluorescein, calcein or the like is used as a marker, and the fluorescence is measured; methods wherein luminescent substances such as lucigenin, luminol, luciferin, or the like are used as a marker, and a developed color is measured; methods wherein pigments such as sulforhodamine are used as a marker and an amount of the released pigment is measured; methods wherein an enzyme substrate such as glucose-6-phosphate is used, an enzyme, such as glucose-6-phosphate dehydrogenase, is used as a color developer, and visible light is measured; and the like, are used.

As a first antibody which is to be linked to liposome, any antibody against an analyte antigen can be used. For example, antiserum obtained from a rabbit, goat, sheep, rat, pig, guinea pig, chicken, mouse or the like immunized with an analyte antigen can be used. Moreover, a monoclonal antibody such as mouse monoclonal antibodies or the like are preferably used. These antibodies can be used in a form of a native antibody molecule, or in a form of a fragment thereof, such as F(ab) or Fab. Processes for the preparation of these polyclonal antisera and monoclonal antibodies are well known, and the above-mentioned antibodies of the present invention can be prepared by a conventional method.

The above-mentioned liposome is linked with antibody molecules via a covalent bond usually using a divalent reagent as a linker. The divalent reagents used in the present invention include dialdehyde compounds such as glutalaldehyde and the like; diisocyanate compounds such as toluene-2,4-diisocyanate, diphenylmethane-4,4'-diisocyanate and the like; diepoxy compounds such as ethylene glycole diglycidyl ether and glyceline diglycidyl ether; bis-diazo compounds such as bis(4-azidophenyl)sulfone, bis(4-azidophenyl)methane and the like; carbodiimide compounds such as 1-ethyl-3-(3-dimethoxy aminopropyl)carbodiimide, N,N'-dicyclohexylcarbodiimide, hexylcarbodiimide, 1-cyclohexyl-3-(2-morpholynyl-4-ethyl) carbodiimide methyl-p-toluenesulfonate; maleimide-carboxylic acid-N-succinimide ester compounds such as N-(m-maleimide benzoic acid)-N-saccinimide ester, 4-(N-maleimide methyl) benzoic acid-N-succinimide ester, 4-(N-maleimide methyl) cyclohexane-1-carboxylic acid-N-succinimide ester and the like; and pyridylthiocarboxylic acid-N-succinimide ester compounds such as 3-(2-pyridylthio) propionic acid-N-succinimide ester and the like. The conditions for the coupling reaction using these divalent regents are well known.

In the present method, as a means for releasing a marker substance from a liposome in an amount relating to an amount of an analyte antigen, a second antibody to the analyte antigen and a third antibody capable of binding directly or indirectly to the second antibody and capable of activating a complement are used. As the second antibody, any antibody which is an antibody to the analyte antigen and binds to an antigen determinant on the analyte antigen different from an antigen determinant to which the first antibody binds can be used. Namely, polyclonal antibody obtained from a rabbit, goat, sheep, rat, pig, guinea pig, chicken, mouse of the like immunized with an analyte antigen, or any of various monoclonal antibodies such as mouse monoclonal antibody can be used. The second antibody, as the first antibody, can be used in an intact form or as various fragments thereof, such as F(ab')$_2$, Fab, or the like.

As the third antibody, various antibodies can be used according to the manner in which they bind to the second antibody. For example, where as the third antibody an antibody capable of directly binding to the second antibody is used, this third antibody is an antibody produced by using the second antibody as an antigen; and such third antibodies include various polyclonal antibodies and monoclonal antibodies. In a preferable embodiment, however, the third antibody indirectly binds to the second antibody. In this embodiment, an antibody to an antigen not relating to the second antibody, or to a hapten is prepared. In this case, the second antibody is a complex antibody comprising an antibody to the analyte antigen, and an antigen or hapten used to prepare the third antibody or material having the same reactivity. This embodiment is most preferable because, as the third antibody, any antibody having a high ability to activate a hapten can be chosen, regardless of the second antibody chosen. As an antigen for the preparation of the third antibody, and therefore, as a partner of the second complex antibody, various kinds of protens or polypeptides, preferably those having a molecular weight of not more than 30,000, may be used. For example, horse radish peroxidase, myoglobin, glutathione-S-transferase, avidin, and various synthetic peptide can be used. According to the most preferable embodiment of the present invention, however, as an antigen for the preparation of the third antibody, a low molecular weight hapten conjugated to an appropriate carrier is used, and as a partner of the second complex antibody, said hapten is used. Namely, as the second antibody "a low molecular weight hapten-conjugated antibody" is used. Such hapten include any materials which are antigenic when conjugated to an appropriate carrier, for example, dinitrobenzenes such as those providing 2,4-dinitrophenyl group (DNP), trinitrobenzenes such as those providing 2,4,6-trinitrophenyl group (TNP); biotins such as those providing biotinoyl or iminobiotinoyl; steroids such as aldosterone, 17-$\beta$-estradiol, tertosterone; hydantoins such as diphenylhydantoin; or fluoresceins such as fluoroisothiocyanate. The process for a production of an antibody using a hapten is well known. Where, as the second antibody, a low molecular weight hapten-conjugated antibody is used, the manner of conjugation of the second antibody and hapten is well known. For example, to link a second antibody and an antigenic protein or polypeptide, for example, difunctional linkers described above for the linkage of liposome and antibody molecule can be used. On the other hand, to link a second antibody and a low molecular weight hapten, the low molecular weight hapten is condensed through the functional group thereof with an amino group, carboxyl group or the like, of the antibody. Alternatively, they are linked through the difunctional linker described above for the linkage of liposome and antibody molecule. The number of the hapten substituents in a hapten-conjugated antibody is preferably 1 to 20 per an antibody molecule.

In both cases where the third antibody is an antibody to the second antibody, and where the third antibody is an antibody to a hapten not relating to the second antibody, the third antibody must have a complement-activating ability. Such antibodies include various polyclonal antibodies and monoclonal antibodies, such as rabbit antibody or mouse monoclonal antibody. These antibodies may be used as an intact antibody or as various kinds of fragments thereof, so long as they maintain the complement-activating ability.

In the present invention, a complement from any animal species can be used, and a complement from guinea pig is preferable.

As reaction media used in carrying out the present method, various kinds of buffers having a pH value of about 5.0 to 10.0, preferably 6.5 to 8.5, for example, gelatin veronal buffer, Hepes buffer, Tris buffer and the like, can be used. The temperature used is not critical and, for example, can be 25° C. to 50° C., preferably 30° C. to 40° C., for example 37° C.

As described above, the present process is carried out by reacting (1) an analyte antigen, (2) a liposome bearing first antibody, (3) a second antibody, (4) a third antibody which binds to the second antibody, and (5) a hapten; and the order of the addition of these reaction components to a reaction mixture is not critical, and they can be added in any order, or may be substantially simultaneously combined. According to a preferable embodiment, first, (1) an analyte antigen, (2) a liposome bearing first antibody, and (3) a second antibody are mixed and the mixture is incubated for a predetermined period to form an antigen-antibody complex, of three components and then to the mixture are added (4) a third antibody and (5) a hapten, and the mixture is incubated for a predetermined period to release a marker. Where this two-step reaction is carried out, for example, the first step is carried out for about 30 minutes, and the second step is carried out for about one hour.

The present invention also relates to a kit for carrying out the above-mentioned method. To carry out the method;

(1) a liposome bearing antibody comprising a first antibody to an analyte antigen and liposome encapsulating a marker therein linked to the antibody;

(2) a second antibody to the analyte antigen;

(3) a third antibody capable of binding directly or indirectly to the second antibody and having an ability to activate a complement; and (4) the complement; are necessary, but since these can be prepared in site where the assay is carried out, the present kit includes not only that containing all the above-mentioned components but also that containing one, two or three of the above-mentioned components. The present kit also can contain buffers for the dilution of the reactants, and if necessary to detect the released marker, can contain reagents for that purpose.

Next, the present invention is described in more detail in the following Examples.

EXAMPLE 1

(a) Preparation of liposomes encapsulating antibody

100 μl of 5 mM dipalmitoylphosphatidylcholine (DPPD), 50 μl of 10 μM cholesterol and 20 μl of 1 mM dithiopyridyl group substituted dipalmitoylphosphatidylethanolamine (DTP-DPPE) were put into an eggplant-shaped flask, and the solvents were evaporated off under a reduced pressure to form a film. After drying for 30 minutes, 100 μl of 0.2 M carboxyfluorescein (CF) solution was added to the mixture, which was then stirred by a vortex mixer to form CF-containing liposomes (MLV). The liposomes were washed by centrifugation. On the other hand, 1 ml of anti-$\alpha_2$PI mouse monoclonal antibody acetylmercaptosuccinylated according to a conventional procedure using acethylmercaptosuccinyl anhydride (concentration; 0.5 mg/ml) was added to the washed liposome to react overnight, and any unreacted antibody was removed by centrifugation to prepare liposomes bearing the antibody.

(b) Preparation of DNP-conjugated antibody

To 200 μl each of 1 mg/ml anti-$\alpha_2$PI mouse monoclonal antibody (MCA2) (recognizing an antigen determinant different from that for the MCA1) in 0.1 M carbonate buffer (pH 8.0), 10, 5, 2.5, 0.25 or 0.62 mg/ml dinitrofluorobenzene (DNP) in dioxane was added, respectively, and a reaction was carried out for 5 hours at room temperature. In this case a ratio of the MCA2 and DNP was MCA2/DNP=1/200, 1/100, 1/50, 1/25, 1/12.5 1/6.25 (W/W). After the reaction, the mixture was dialyzed against a phosphate-buffered physiological saline to prepare an anti-$\alpha_2$PI mouse monoclonal antibody conjugated with DNP (DNP-MCA2) at a ratio described above.

(c) Liposome immunoassay (1)

Figure 2:
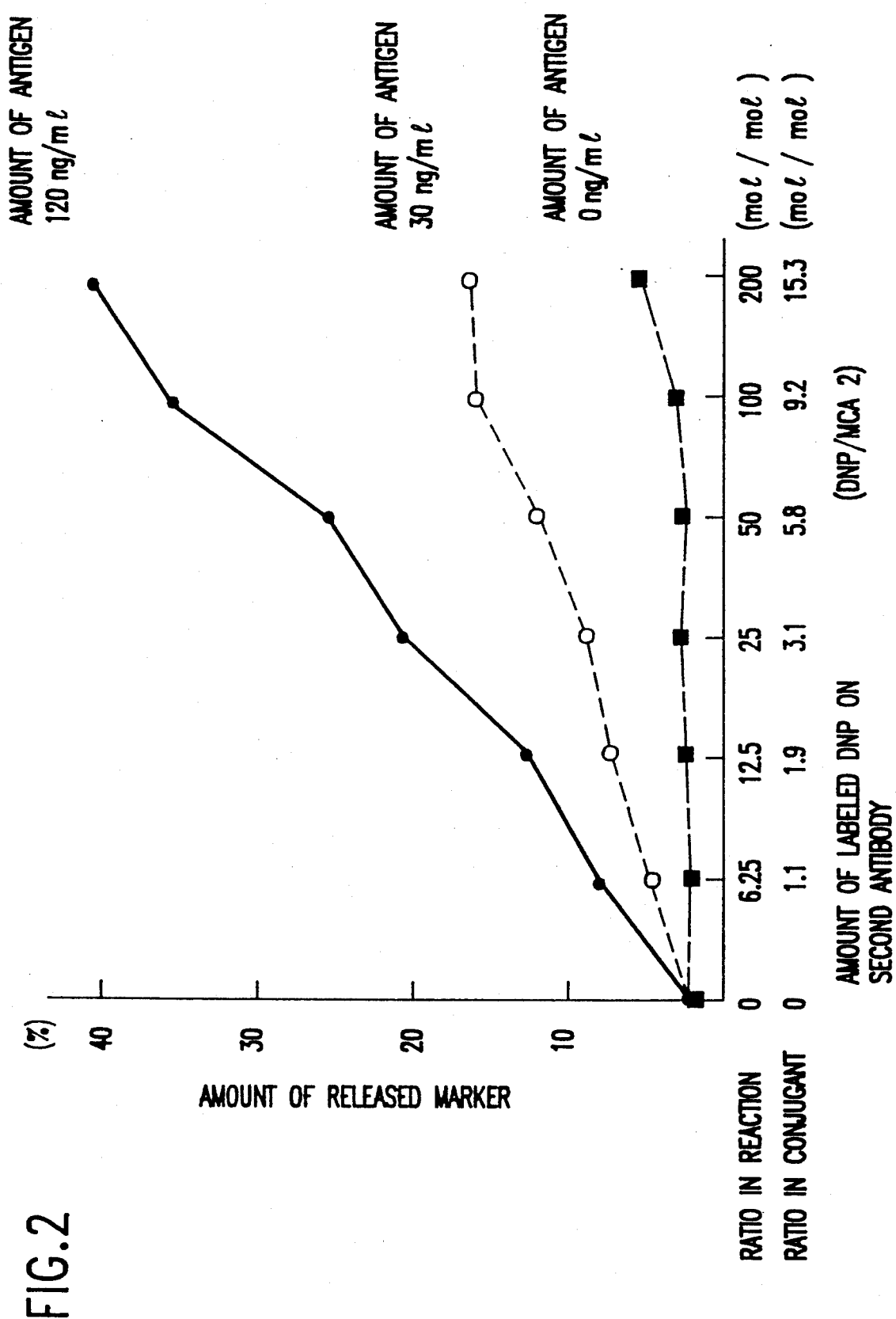
FIG. 2 is a graph showing the relationship between an amount of the DNP bound to the second antibody and an amount of the released marker.

25 μl each of 120 ng/ml, 30 ng/ml, and 0 ng/ml $\alpha_2$PI, which is an analyte antigen, 5 μl of a 50-fold diluted MCA1-sensitized liposome suspension (in gelatin veronal buffer, pH 7.4, 5 mM $Mg^{++}$, 5 mM $Ca^{++}$), and 25 μl of 5 μg/ml DNP-conjugated MCA2 (and non-DNP-conjugated MCA2 as a control) were mixed, and after incubation at 37° C. for 30 minutes, to the reaction mixture were added 25 μl of a rabbit anti-DNP antibody (concentration; 20 μg/ml) and 25 μl of a guinea pig complement $3CH_{50}$, and the mixture was incubated at 37° C. for one hour, and the fluorescence was measured by a MTP-32 fluorescence microplate reader. The results are shown in FIG. 2. An amount of the released marker (fluorescence) is clearly proportional to an amount of conjugated DNP, revealing that the DNP-conjugated antibody is effectively involved in the present immune reaction.

(d) Liposome immunoassay (2)

Liposome immune lysis assay (LILA) using a DNP-conjugated second antibody.

Figure 3:
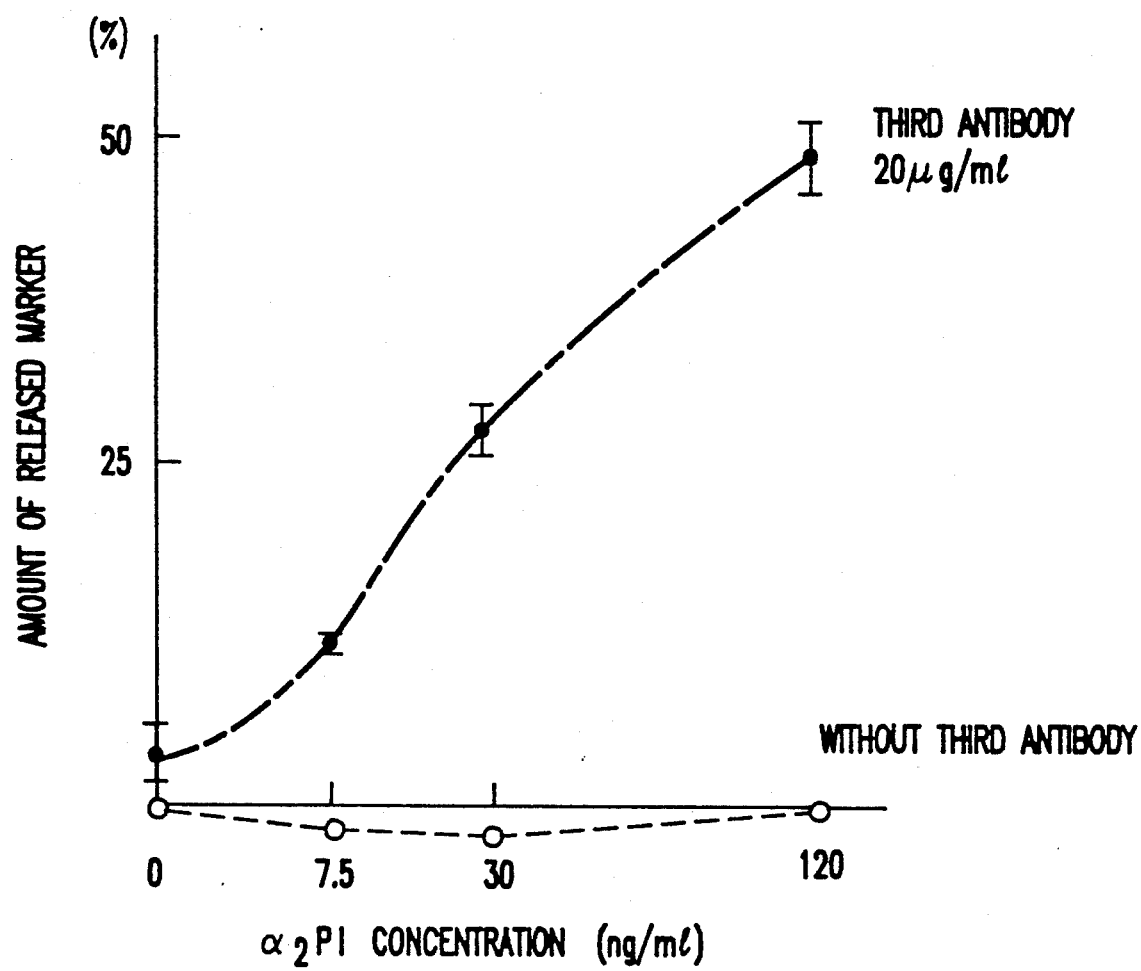
FIG. 3 is a graph showing an example of a calibration curve for measuring an analyte antigen, $\alpha_2$ plasminogen inhibitor ($\alpha_2$PI) according to the present invention.

To 25 μl each of an antigen ($\alpha_2$PI) solution having a concentration of 120, 60, 30, 15, or 7.5 ng/ml were added 5 μl of a diluted liposome suspension bearing the MCA1, and 25 μl of DNP-conjugated second antibody (mouse monoclonal antibody (MCA2), MCA2/DNP=1/200 (ratio in reaction)=1/15.3 (ratio in conjugant)), and after a reaction was carried out at 37° C. for 25 μl, 25 μl of a rabbit anti-DNP antibody as a third antibody and 25 μl of a guinea pig complement were added, and a reaction was carried out 37° C. for one hour. Moreover, as a comparative experiment, the LILA was carried out not using the rabbit anti-DNP antibody. The results are shown in FIG. 3, from which it is seen that a reaction proceeds in an antigen ($\alpha_2$ PI) specific manner.

Figure 4:
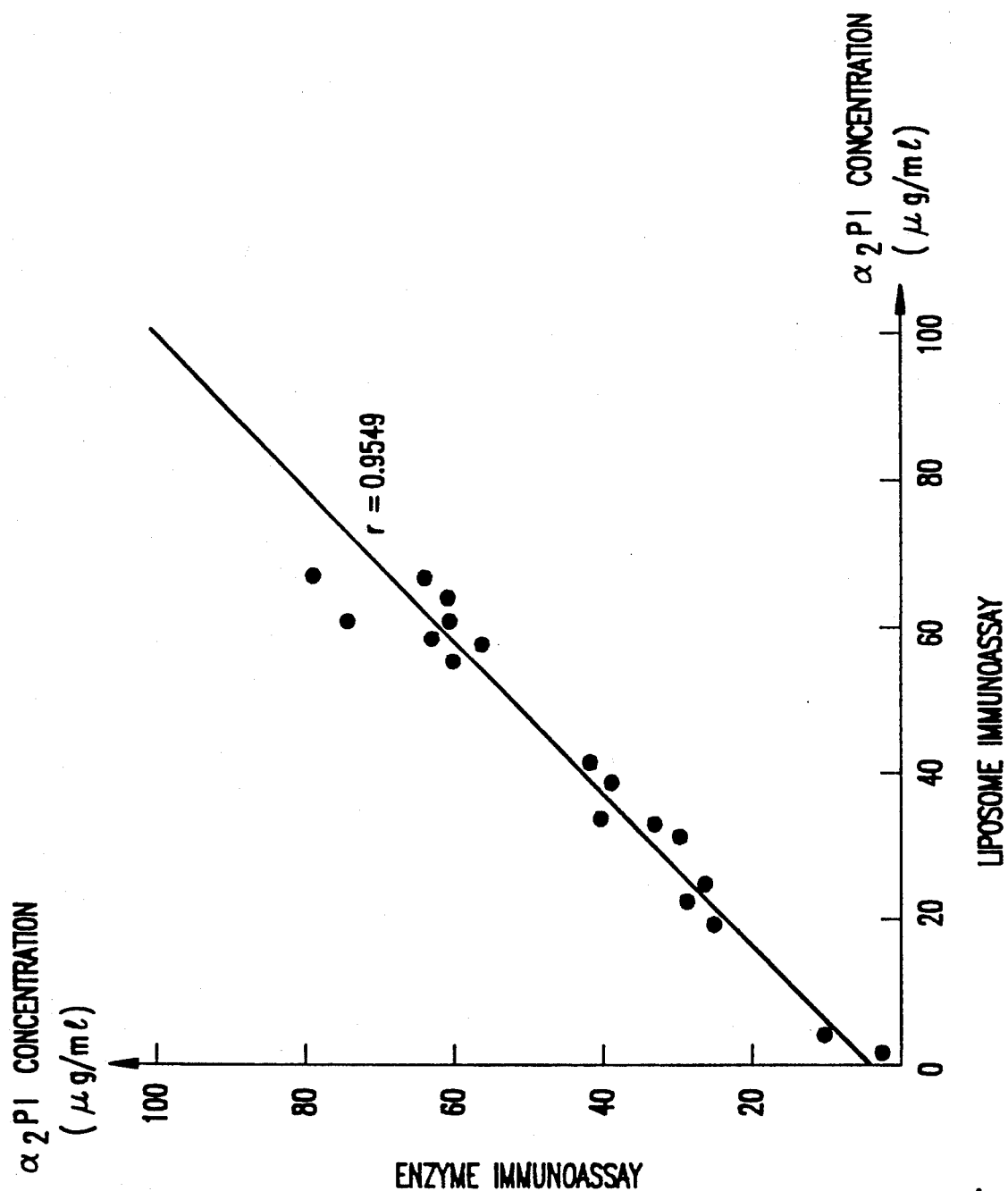
FIG. 4 is a graph showing the correlation between an value of $\alpha_2$PI obtained by measurement according to the present invention and a value of $\alpha_2$PI obtained by measurement according to a conventional immunoassay.

(e) Comparison between the present liposome immunoassay and conventional enzyme immunoassay Serum $\alpha_2$PI level of 18 patients having disseminated intravascular coagulation (DIC) was measured using the present assay. As seen from FIG. 4, wherein the result is compared with a result from a conventional enzyme immunoassay for $\alpha_2$PI, there is a good correlation therebetween as represented by r=0.9549 revealing that the present method specifically measures the $\alpha_2$PI.

EXAMPLE 2

(a) To 1 ml of anti-$\alpha_2$PI monoclonal antibody (MCA-2) used in Example 1(b) having a concentration of 1 mg/ml, was added 0.2 ml of maleimidobenzoyl succinimide ester (MBS) in 30 μl of dimethylfolmamide (DMF), and they were reacted at 25° C. for 30 minutes, and passed through a Sephadex G-25 column ($\phi$10 mm×25 cm) to obtain MBS-acylated MCA-2. This MBS-conjugated MCA-2 was mixed with 2.8 mg/0.2 cc of horse radish peroxidase (HRP), and they were reacted at 4° C. overnight and passed through an Ultro gel ACA34 (LKB) column ($\phi$1.5 cm ×25 cm) to prepare an HRP-conjugated MCA-2.

Figure 5:
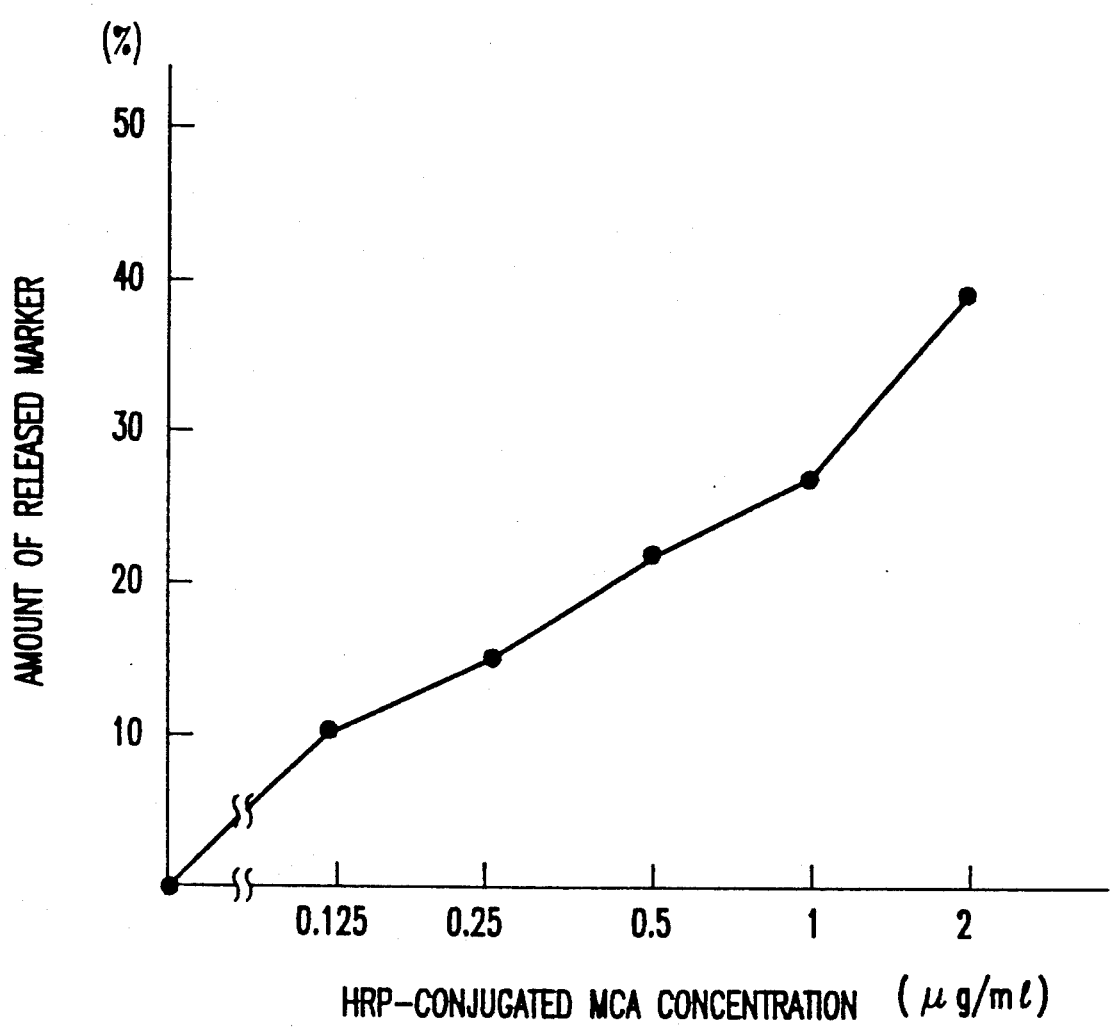
FIG. 5 is a graph showing the relationship between a concentration of the second antibody and an amount of the released maker where an anti-$\alpha_2$PI mouse monoclonal antibody (MCA-2) conjugated to horse radish peroxidase (HRP) is used as the second antibody, antigen ($\alpha_2$PI) concentration was 120 ng/ml; and, FIG. 6 is a graph showing the relationship between a concentration of the second antibody in a reaction mixture and an efficiency of the release of the marker where different second antibodies are used. In the figure, A represents a result obtained where the distance between a binding site of the first antibody and a binding site of the second antibody on an antigen polypeptide is relatively small on the basis of a primary structure of the peptide, and B represents a result where the distance between a binding site of the first antibody and a binding site of the second antibody is relatively large.

(b) The LILA was carried out in substantially the same manner as Example 1(c), except that a rabbit anti-HRP antibody was used instead of the rabbit anti-DNP antibody. As shown in FIG. 5, at 120 mg/ml $\alpha_2$PI, the LILA proceeded in a manner dependent on the HRP-MCA2, which is a second antibody.

EXAMPLE 3

Figure 6A:
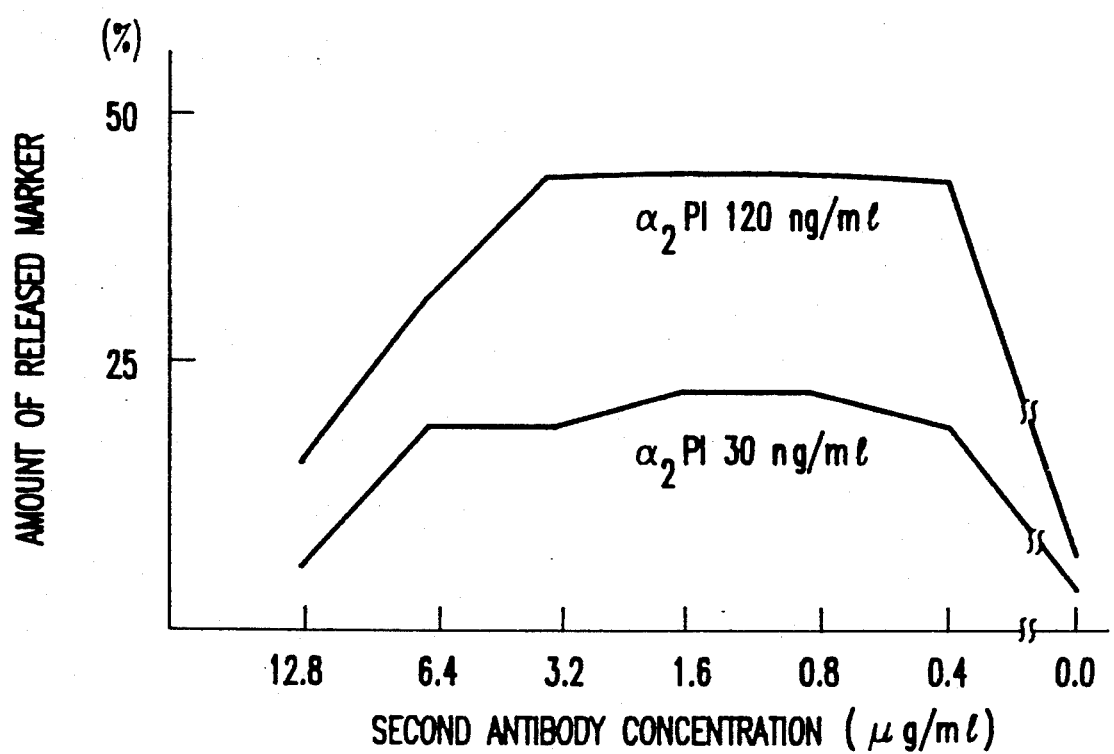
Figure 6B:
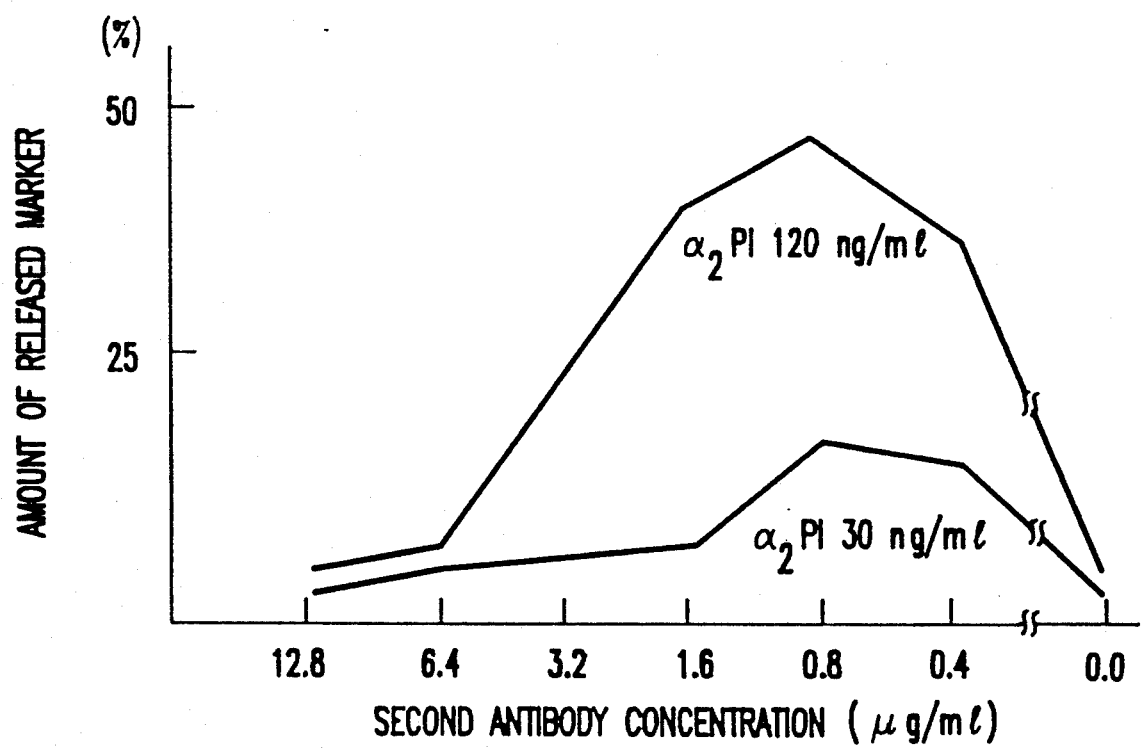

To examine an effect of the kind of second antibodies on the measurement, in addition to the DNP-conjugated MCA-2 prepared in Example 1(b) (FIG. 6A), DNP-conjugated MCA-3 similarly prepared (FIG. 6B) was used to observe the relationship between a second antibody concentration and an amount of released marker. As seen from FIG. 6, where the MCA-3 was used, a range of the optional concentration thereof was narrower than that of the MCA-2, but since the present method can be carried out using a predetermined optimum concentration of the second antibody, the use of the MCA-3 is not disadvantageous.

According to Mimuro et al., Blood, Vol. 69, No. 2 (1987) pp 446–453, the MCA-3 used as a first antibody binds to a central site on an $\alpha_2$PI antigen polypeptide molecule, the MCA-2 binds at a site on N-terminal site of the peptide considerably far from the site for the MCA-1, and the MCA-3 binds at a site near the site for the MCA-1 and C-terminal side therefrom. Therefore, the above-mentioned result shows that the present method can be successfully used regardless of the position of an antigen determinant for a second antibody.

EXAMPLE 4

Assay kit

Reagent A: 1 ml of suspension comprising a liposome bearing antibody comprising a first antibody to an analyte antigen $\alpha_2$PI and liposome encapsulating a marker carboxyfluorescein therein linked to the antibody, and TNP (haptenized) second antibody (in test tube A):

Reagent B: Lyophilized powder of guinea pig complement (in test tube B); and

Reagent C: Lyophilized tablet of rabbit anti-TNP antibody (tablet C).

Method of use

5 μl of a sample was added to the test tube A, and after the mixture was incubated at 37° C. for 30 minutes, the tablet C was added to the test tube. Next, the inlet of the test tube A was attached to the inlet of the test tube B, and they were slowly reversed to dissolve the reagents B and C, and after the whole was incubated at 37° C. for one hour, the fluorescence was measured.

We claim:

1. A liposome immunoassay method comprising the steps of:

(a) reacting a sample containing an analyte antigen with a first antibody which specifically binds said analyte antigen, wherein said first antibody is bound to a liposome and wherein said liposome encapsulates a marker, so as to form a first complex;

(b) reacting said first complex with a second antibody which specifically binds said analyte antigen and does not activate complement, so as to form a second complex;

(c) reacting said second complex with a third antibody which specifically binds said second antibody but does not bind said analyte antigen, wherein said third antibody activates complement, so as to form a third complex;

(d) reacting said third complex with complement; and (e) measuring the amount of marker released from the liposome in said third complex as a result of step (d) so as to measure the amount of analyte antigen in said sample.

2. A method according to claim 1, wherein the third antibody is a rabbit antibody.

3. A method according to claim 1, wherein the third antibody is a mouse monoclonal antibody.

4. A method according to claim 1, wherein the third antibody is an antibody recognizing a hapten of less than 30,000 molecular weight, and the second antibody is an antibody which has been linked to said hapten.

5. A method according to claim 4, wherein said low molecular weight hapten is selected from the group consisting of dinitrobenzenes, trinitrobenzenes, biotins, steroids, hydantoins and fluoresceins.

6. The method of claim 5, wherein said steroid is selected from the group consisting of aldosterone, estradiol and progesterone.

7. A method according to claim 1, wherein said marker is selected from the group consisting of fluorescent compounds, pigmented compounds, luminescent compounds, enzymes and enzyme substrates.

8. The method of claim 1, wherein said analyte antigen is a clotting factor.

9. The method of claim 1, wherein said analyte antigen is a clot dissolving factor.

10. The method of claim 1, wherein said analyte antigen is a cancer-specific molecule.

11. The method of claim 1, wherein said analyte antigen is an inflammation marker.

12. The method of claim 1, wherein said analyte antigen is a hormone.

13. The method of claim 1, wherein said analyte antigen is a molecule related to osteometabolism.

14. The method of claim 1, wherein said analyte antigen is a molecule of a component of the immune system.

15. A kit for liposome immunoassay comprising:
(1) a liposome bearing antibody comprising a first antibody to an analyte antigen and liposome encapsulating a marker therein linked to the antibody;
(2) a second antibody to the analyte antigen; and
(3) a third antibody capable of binding directly or indirectly to the second antibody and having an ability to activate a complement.

16. The kit of claim 15 further comprising, (4) complement.

* * * * *